United States Patent [19]
Alexander

[11] Patent Number: 5,846,228
[45] Date of Patent: Dec. 8, 1998

[54] SAFETY SYRINGE FOR FLUID COLLECTION

[75] Inventor: Gary E. Alexander, Baton Rouge, La.

[73] Assignee: Medisys Technologies, Inc., Baton Rouge, La.

[21] Appl. No.: 746,580

[22] Filed: Nov. 14, 1996

[51] Int. Cl.⁶ ..................................................... A61M 5/32
[52] U.S. Cl. ........................................... 604/195; 604/194
[58] Field of Search ...................... 604/198, 263, 604/192, 187, 210, 211, 222, 228, 164, 195, 194

[56] References Cited

U.S. PATENT DOCUMENTS

| | | |
|---|---|---|
| 3,094,122 | 6/1963 | Gauthier et al. .......................... 128/221 |
| 4,026,287 | 5/1977 | Haller . |
| 4,197,846 | 4/1980 | Bucalo . |
| 4,425,120 | 1/1984 | Sampson . |
| 4,464,171 | 8/1984 | Garwin ..................................... 604/164 |
| 4,581,021 | 4/1986 | Landau et al. . |
| 4,636,202 | 1/1987 | Lowin et al. . |
| 4,702,738 | 10/1987 | Spencer . |
| 4,737,150 | 4/1988 | Baeumle et al. . |
| 4,846,785 | 7/1989 | Cassou et al. . |
| 4,846,799 | 7/1989 | Tanaka et al. ........................... 604/158 |
| 4,850,996 | 7/1989 | Cree . |
| 4,863,434 | 9/1989 | Bayless . |
| 4,863,435 | 9/1989 | Sturman et al. . |
| 4,874,382 | 10/1989 | Lindemann et al. . |
| 4,875,896 | 10/1989 | Kurtz . |
| 4,883,471 | 11/1989 | Michel . |
| 4,883,472 | 11/1989 | Michel . |
| 4,892,107 | 1/1990 | Haber . |
| 4,894,055 | 1/1990 | Sudnak . |
| 4,909,791 | 3/1990 | Norelli . |
| 4,909,792 | 3/1990 | Norelli . |
| 4,923,445 | 5/1990 | Ryan . |
| 4,929,237 | 5/1990 | Medway . |
| 4,935,014 | 6/1990 | Haber . |
| 4,935,016 | 6/1990 | Deleo ....................................... 604/263 |
| 4,936,830 | 6/1990 | Verlier . |
| 4,944,723 | 7/1990 | Haber et al. . |
| 4,966,592 | 10/1990 | Burns et al. . |
| 4,966,593 | 10/1990 | Lennox . |
| 4,969,877 | 11/1990 | Kornberg . |
| 4,973,316 | 11/1990 | Dysarz ..................................... 604/195 |
| 4,973,317 | 11/1990 | Bobrove ................................... 604/198 |

(List continued on next page.)

FOREIGN PATENT DOCUMENTS 8908468  3/1989  Japan .

OTHER PUBLICATIONS

U.S. Ser. No. 08/727,756, Alexander, filed Oct. 8, 1996.

Primary Examiner—Michael Powell Buiz
Assistant Examiner—A. T. Nguyen
Attorney, Agent, or Firm—Roy, Kiesel & Tucker

[57] ABSTRACT

The invention comprises a safety syringe having a barrel containing a fluid receiving cavity, a plunger, a needle and a blunt sheath. The needle is connected to the plunger so that when the plunger is retracted, the needle is retracted. The sheath extends from the barrel and is circumferentially positioned about the needle. When fully extended, the sharp end of the needle extends from the sheath, but upon retraction, the sheath covers the sharp end. The external diameter of the sheath is sized to allow the sheath to be inserted hypodermically with the needle. Upon insertion of the needle and sheath into the patient, the plunger may be withdrawn. This will create a vacuum and will cause the needle to be retracted into the sheath. Fluids will flow through the sheath and the needle into the fluid receiving cavity because of the vacuum. When fluid collection is complete, the syringe may be withdrawn with the needle already safely encased in the blunt sheath. Fluids may be expelled from the syringe through the needle and the sheath by depressing the plunger. A locking device stops the needle from advancing beyond the end of the sheath, preventing both reuse and accidental sticks without interfering with the expulsion of fluids.

21 Claims, 4 Drawing Sheets

U.S. PATENT DOCUMENTS

| | | | |
|---|---|---|---|
| 4,976,701 | 12/1990 | Ejlersen et al. | 604/192 |
| 4,982,842 | 1/1991 | Hollister | 604/198 |
| 4,986,819 | 1/1991 | Sobel | 604/198 |
| 4,994,041 | 2/1991 | Dombrowski et al. | 604/164 |
| 5,015,240 | 5/1991 | Soproni et al. | 604/192 |
| 5,026,353 | 6/1991 | Bartman | 604/192 |
| 5,032,117 | 7/1991 | Motta | 604/88 |
| 5,051,109 | 9/1991 | Simmon | 604/263 |
| 5,067,942 | 11/1991 | Jaffe et al. | 604/110 |
| 5,092,851 | 3/1992 | Ragner | 604/192 |
| 5,092,852 | 3/1992 | Poling | 604/192 |
| 5,098,401 | 3/1992 | De Lange | 604/192 |
| 5,104,384 | 4/1992 | Parry | 604/192 |
| 5,122,123 | 6/1992 | Vaillancourt | 604/192 |
| 5,135,507 | 8/1992 | Haber et al. | 604/187 |
| 5,151,088 | 9/1992 | Allison | 604/192 |
| 5,205,825 | 4/1993 | Allison et al. | 604/110 |
| 5,282,792 | 2/1994 | Imbert | 604/187 |
| 5,300,038 | 4/1994 | Haber et al. | 604/187 |
| 5,306,258 | 4/1994 | de la Fuente | 604/198 |
| 5,314,503 | 5/1994 | Bobrove et al. | 604/164 |
| 5,342,320 | 8/1994 | Cameron | 604/192 |
| 5,370,628 | 12/1994 | Allison et al. | 604/192 |
| 5,385,555 | 1/1995 | Hausser | 604/192 |
| 5,460,611 | 10/1995 | Alexander | 604/110 |

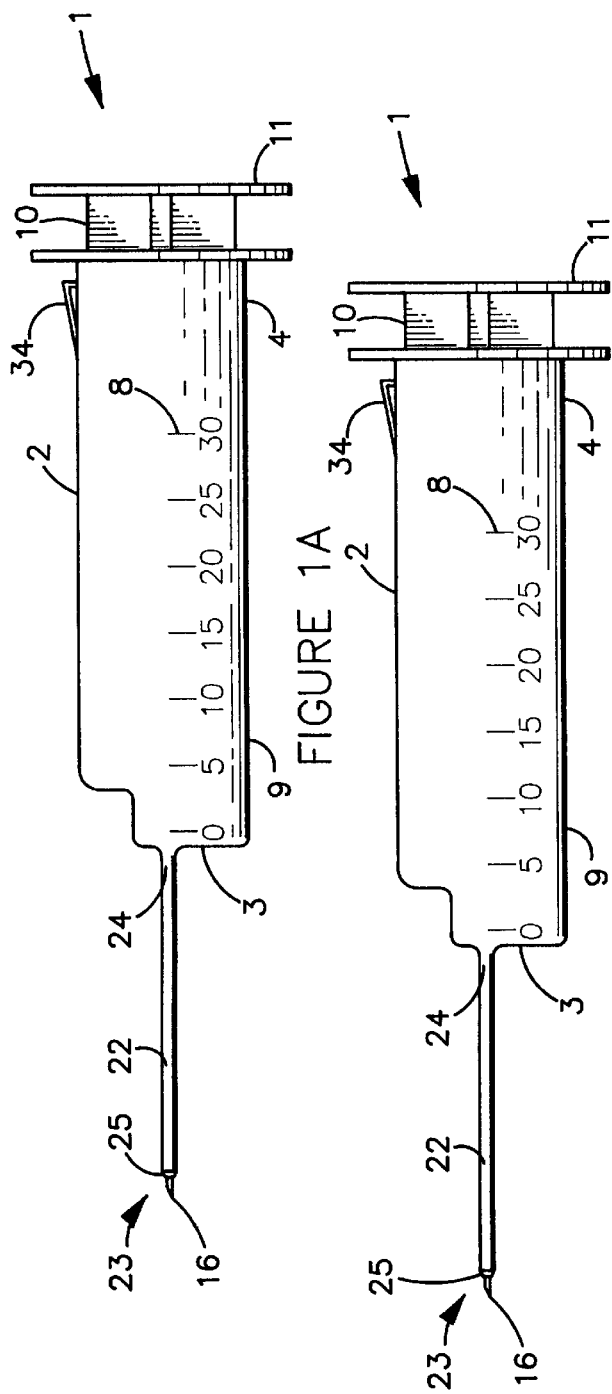
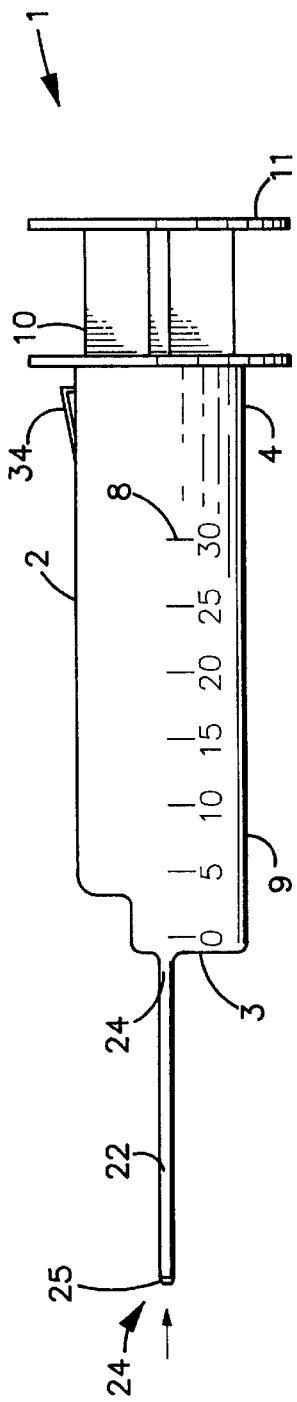
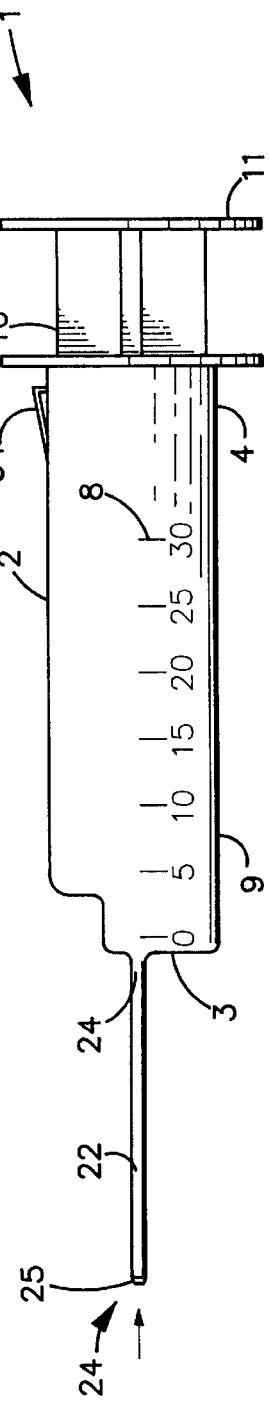

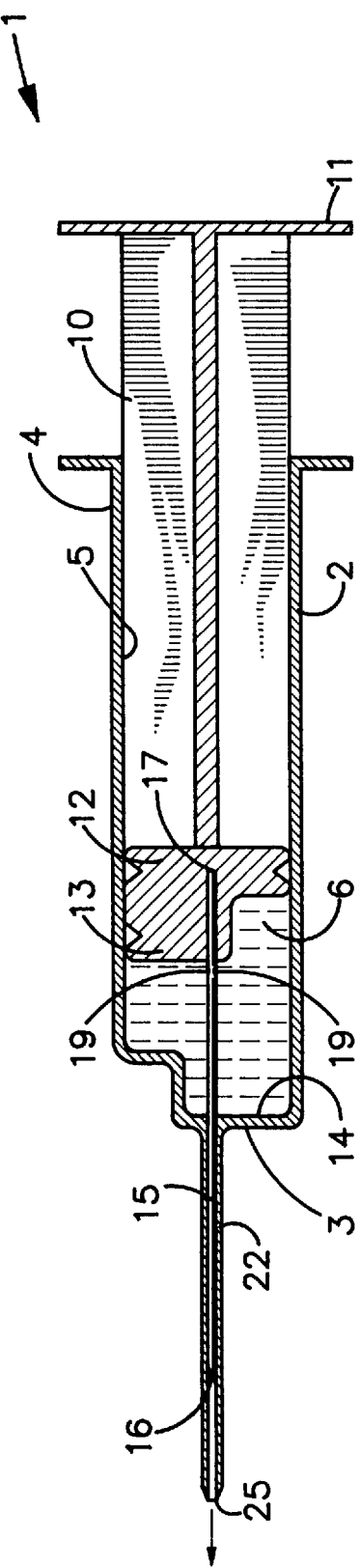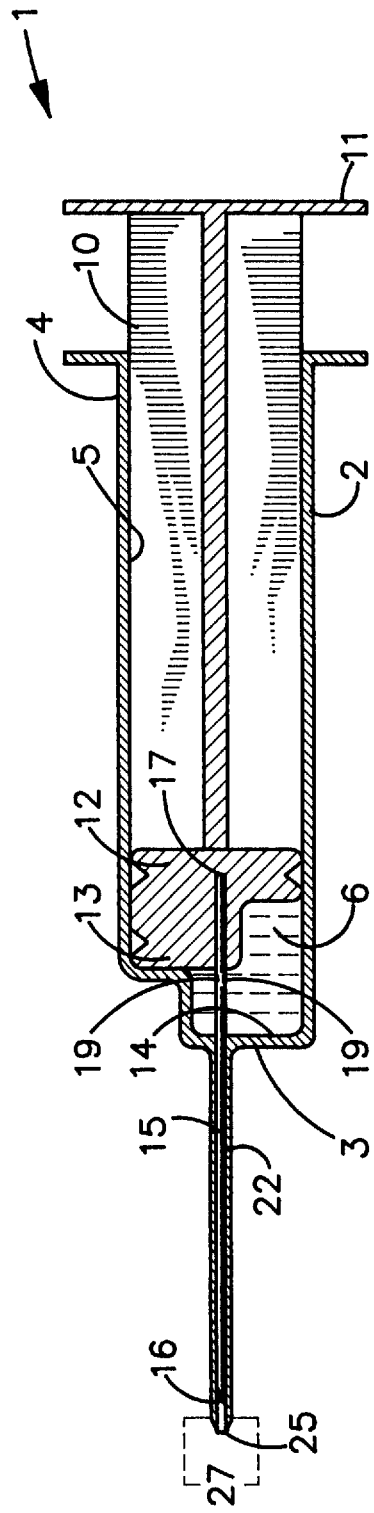

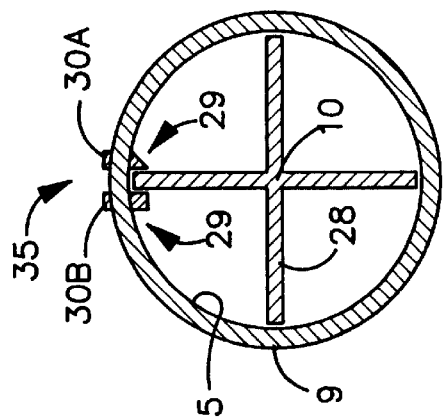
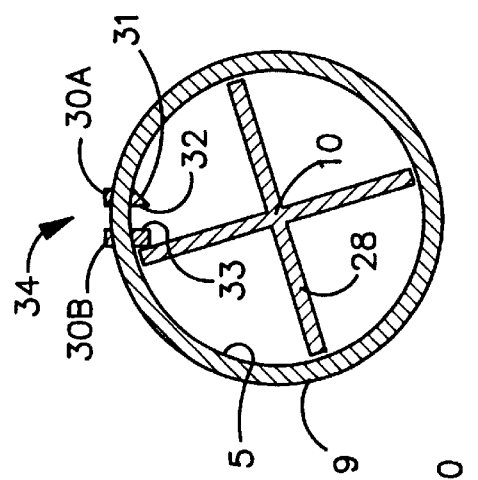
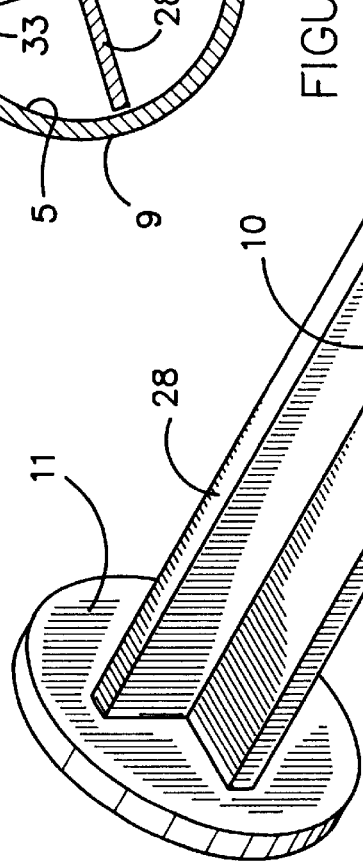

ized so that

SAFETY SYRINGE FOR FLUID COLLECTION

BACKGROUND OF THE INVENTION

1. Field of the Invention

The invention relates to safety syringes in general and to blood collection safety syringes in particular.

2. Prior Art

The risk of contracting diseases such as HIV or hepatitis from accidental sticks with dirty needles is a potentially deadly hazard for medical professionals. Many syringe designs have been created that attempt to avoid or minimize this risk. A shortcoming common to many syringes in the prior art is that the sharp end of the needles are often exposed during the period immediately following their removal from the patient, providing a dangerous window of opportunity for an accidental stick with a contaminated needle. Another difficulty with the prior art syringes is their inability to be used conveniently for fluid collection. In using traditional non-safety syringes for blood collection, the contents of the syringe are usually emptied into a vial by placing the needle into the vial and depressing the plunger. The blood may then be removed from the vial for analysis as desired. However, in many of the prior art safety syringes, it is difficult to expel the contents of the syringe simply by depressing the plunger once the needle has been covered. This can lead to the safety mechanisms not being engaged until after the syringe has been emptied, increasing the opportunities for an accidental stick. Accordingly, a safety syringe that meets the following objectives is disclosed.

OBJECTS OF THE INVENTION

It is an object of the invention to help prevent the transmission of AIDS and other diseases through accidental sticks with contaminated needles.

It is an object of the invention to provide a safety syringe which minimizes the chances of an accidental stick with a contaminated needle.

It is an object of the invention to provide a safety syringe capable of collecting blood and other fluids.

It is another object of the invention to provide a safety syringe in which the needle is covered prior to its removal from the patient.

It is another object of the invention to provide a safety syringe that operates in a substantially similar fashion to a conventional syringe.

It is yet another object of the invention to provide a safety syringe whose contents may be expelled by depressing the plunger while keeping the needle covered.

It is still another object of the invention to provide a safety syringe which is designed to prevent reuse.

SUMMARY OF THE INVENTION

The invention comprises a safety syringe having a barrel, a plunger, a needle and a blunt sheath. The needle is functionally connected to the plunger so that when the plunger is retracted, the needle is retracted. The sheath is attached to the barrel and the needle passes through the sheath so that the sheath is circumferentially positioned about the needle. The sheath is sized and positioned so that the sharp end of the needle extends from the sheath when the needle is fully extended. However, upon retraction, the sharp end of the needle is contained within the sheath. The external diameter of the sheath, or at least its tip end, is sized so that the sheath may be inserted hypodermically or intravenously with the needle in much the same way a catheter is inserted. The external diameter of the sheath at its tip end should preferably be between about 110% and 150% of the external diameter of the needle. Upon insertion of the needle and sheath into the appropriate location in the patient, the plunger may be withdrawn. This will create a vacuum and will cause the needle to be retracted into the sheath. The sheath will provide fluid passage to the needle which in turn will provide passage into the fluid receiving cavity contained within the barrel. Alternatively, the sheath may provide passage into the fluid receiving cavity either instead of or in conjunction with the needle. The vacuum will cause the fluids surrounding the end of the sheath to flow through the sheath and the needle into the fluid receiving cavity. If the needle and sheath have been inserted into a blood vessel, the body's blood pressure may also cause this flow. Once the desired amount of fluid has been obtained, the syringe may be removed from the body. The needle will already be safely encased in the blunt sheath upon withdrawal. Fluids may be expelled from the syringe through the needle and the sheath simply by depressing the plunger. Use of a simple locking device may prevent the sharp end of the needle from being extended beyond the end of the sheath, thereby preventing both reuse and accidental sticks without interfering with the use of the plunger to expel fluids from the syringe.

BRIEF DESCRIPTION OF THE DRAWINGS

FIG. 1A is a side view of a preferred embodiment of the safety syringe prior to insertion of the needle and the sheath into the patient.

FIG. 1B is a side view of a preferred embodiment of the safety syringe after insertion of the needle and the sheath into the patient.

FIG. 1C is a side view of a preferred embodiment of the safety syringe during withdrawal of fluids from the patient. The directional arrow shown in FIG. 1C illustrates the fluid flow into the syringe.

FIG. 3A is a cross-sectional view of a preferred embodiment of the safety syringe in the "locked" position during expulsion of fluid from the safety syringe. The directional arrow shown in FIG. 3A illustrates the fluid flow out of the syringe.

FIG. 3B is a cross-sectional view of a preferred embodiment of the safety syringe in the "locked" position after the expulsion of fluid from the safety syringe.

FIG. 4 is a perspective view of a preferred embodiment of the plunger, the washer end of the plunger, and the needle.

FIG. 5A is a cut away top view of a preferred embodiment showing one preferred means for locking the safety syringe in the safe position.

FIG. 5B is a cut away top view of the preferred embodiment illustrated in FIG. 5A wherein the plunger has been rotated counter-clockwise about its longitudinal axis approximately ¼ turn.

DETAILED DESCRIPTION OF THE PREFERRED EMBODIMENTS OF THE INVENTION

Figure 2A:
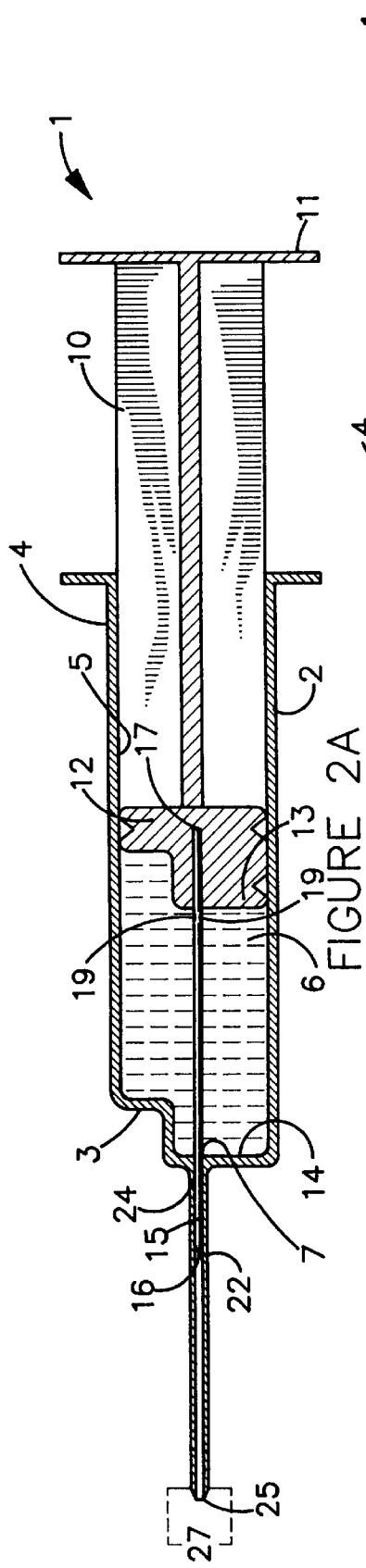
FIG. 2A is a cross-sectional view of a preferred embodiment of the safety syringe during withdrawal of fluid from the patient.

A safety syringe 1 is disclosed. Safety syringe 1 is comprised of a substantially hollow barrel 2 having a needle end 3 and a plunger end 4. In a preferred embodiment, a cylindrical interior wall 5 extends from needle end 3 to plunger end 4, defining a fluid receiving cavity 6. A needle aperture 7 is contained in needle end 3, and preferably in the center of needle end 3. In one embodiment, a grommet (not shown) for providing a fluid tight seal between needle 15 (discussed below) and needle end 3 is contained within needle aperture 7. In a preferred embodiment, calibrated measurement lines 8 are marked on exterior wall 9. In a preferred embodiment, barrel 2 is made of transparent or translucent plastic.

Figure 2B:
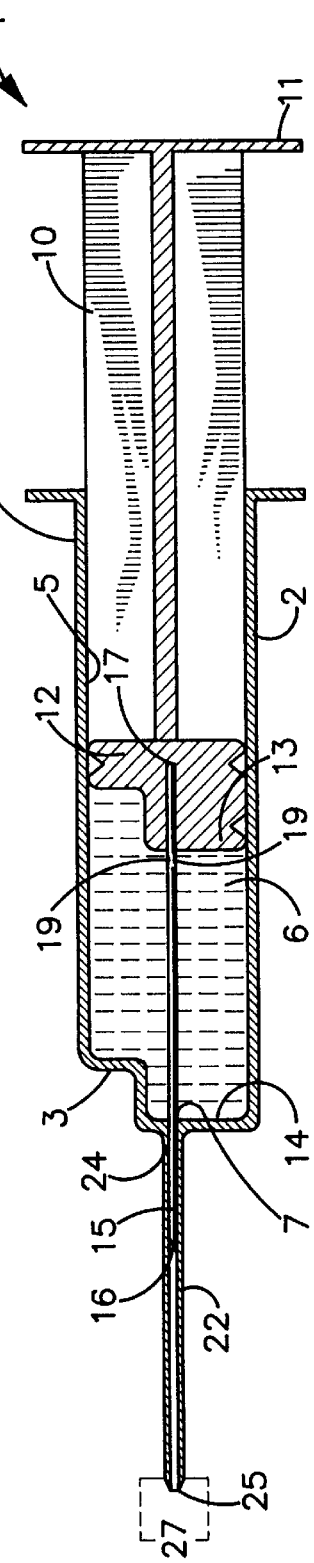
FIG. 2B is a cross-sectional view of a preferred embodiment of the safety syringe after removal of the syringe from the patient.
Figure 2C:
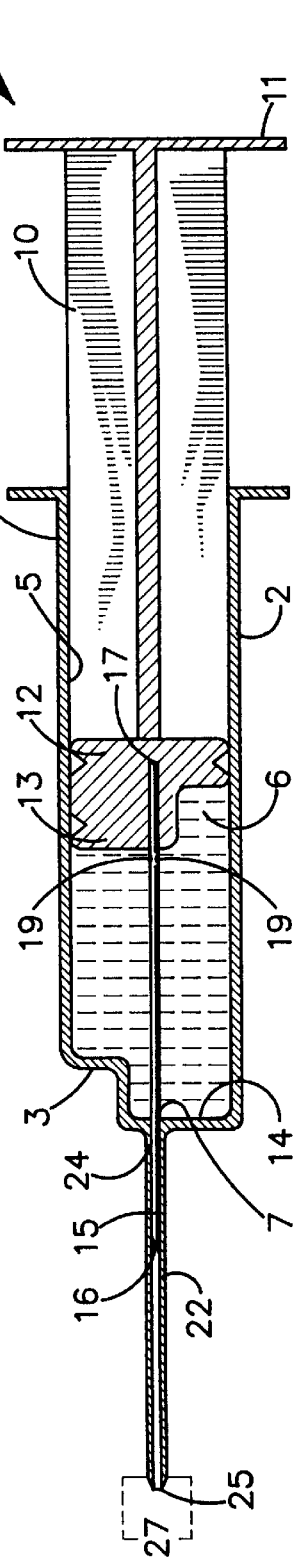
FIG. 2C is a cross-sectional view of a preferred embodiment of the safety syringe after rotation into the "locked" position.

A plunger 10 fits within barrel 2. Plunger 10 has a thumb end 11 and a washer end 12. Washer end 12 is sized to engage interior wall 5 of barrel 2 so that a substantially fluid tight seal is created between washer end 12 and interior wall 5. In a preferred embodiment, washer end 12 is made of or covered with rubber while plunger 10 is made of plastic. Upon insertion of plunger 10 into barrel 2, the volume of fluid receiving cavity 6 may be varied by operation of plunger 10. In one preferred embodiment, washer end 12 of plunger 10 contains a projection 13. In this preferred embodiment, needle end 3 of barrel 2 is recessed to match projection 13 as shown in FIGS. 2, 3, and 4. In this preferred embodiment, washer end 12 of plunger 10 can be advanced the full length of barrel 2 only when projection 13 and recess 14 are aligned. Although the figures illustrate a "pie slice" configuration for projection 13 and recess 14, other configurations are also contemplated. One such configuration would include a centrally located ovally shaped projection 13 and a matching recess 14 (not shown). Ultimately, the goal in designing projection 13 and recess 14 is that the two should allow plunger 10 to advance fully only when they are in alignment and that rotation of plunger 10 about its longitudinal axis should take them out of alignment.

In a preferred embodiment, thumb end 11 of plunger 10 is configured to facilitate the use of thumb end 11 to effect the rotation of plunger 10 about its longitudinal axis. Such configurations may include designing thumb end 11 to contain a knurled knob to facilitate gripping and turning. Another contemplated configuration would entail providing thumb end 11 with a "T" shape, again to facilitate gripping and turning. Finally, this purpose might also be furthered by serating the edges of thumb end 10.

A needle 15 having a sharp end 16 and a plunger end 17 extends from washer end 12 of plunger 10, and preferably from the center of washer end 12. Needle 15 should be positioned to align with needle aperture 7 when plunger 10 is inserted into barrel 2 so that needle 15 will extend through needle aperture 7. Needle 15 should be connected to plunger 10 so that retraction of plunger 10 will retract needle 15 and so that advancement of plunger 10 will advance needle 15.

Needle 15 is hollow and contains a first needle opening 18 at sharp end 16 which provides fluid passage into the hollow center of needle 15. One or more second needle openings 19 may be provided in needle 15 and should also provide fluid passage into the hollow center of needle 15. Second needle openings 19 should preferably be provided below but proximate to washer end 12 so that fluid that flows through needle 15 may enter fluid receiving cavity 6. Preferably, the combined surface area of second needle openings 19 should at least equal the surface area of first needle opening 18. In one preferred embodiment, second needle openings 19 are provided in needle 15 by cutting holes in needle 15. In another embodiment, a U-shaped curve is formed in needle 15 near plunger end 17 which is left open, like sharp, end 16. In this embodiment, needle 15 is attached to washer end 12 at the U-shaped curve so that open plunger end 17 allows fluids flowing through needle 15 to enter fluid receiving cavity 6. Needle 15 is preferably made of stainless steel.

In an alternative embodiment, a solid lance (not shown) may be used in place of needle 15. When lance 20 is used, grommet 21 should not be used because sheath 22 (discussed below) must provide fluid passage into fluid receiving cavity.

A hollow sheath 22, having a barrel end 24 and an open tip end 25, extends from needle end 3 of barrel 2. In one preferred embodiment, sheath 22 and barrel 2 are molded from a single piece of plastic or other material. Barrel end 24 of sheath 22 is aligned with needle aperture 7 in needle end 3 so that when needle 15 is extended through needle aperture 7, needle 15 will be contained within sheath 22. Tip end 25 should not be sharp so that sheath 22 can perform its primary function of preventing accidental sticks with needle 15. In a preferred embodiment tip end 25 may be tapered.

Needle 15 has an extended position 23 that it enters when plunger 10 is fully extended. Sheath 22 should be sized so that sharp end 16 of needle 15 is exposed when needle 15 is in extended position 23. Needle 15 also has a retracted position 24 that it enters as needle 15 is retracted. The retracted position 24 is defined as beginning at that point where sharp end 16 of needle 15 is first completely contained within sheath 22. The distance between extended position 23 and retracted position 24 will depend upon the relative lengths of needle 15 and sheath 22. In a preferred embodiment, the distance between extended position 23 and retracted position 24 will be about ⅛ of an inch. In a preferred embodiment, needle 15, plunger 10, barrel 2, and sheath 22 should be sized so that ordinary retraction of plunger 10 will not result in needle 15 being completely withdrawn from sheath 22.

In a preferred embodiment, the connection between sheath 22 and needle end 3 around needle aperture 7 is fluid tight. In this embodiment, sheath 22 will provide fluid passage into fluid receiving cavity 6 via needle aperture 7. This passage may work in conjunction with that provided by needle 15 such that any fluid that flows around needle 15 into sheath 22 will still be able to enter fluid receiving cavity 6. Alternatively, this passage may operate in place of the passage provided by needle 15 as will be the case in the embodiments using lance 20 rather than needle 15. Of course, for sheath 22 to provide fluid passage into fluid receiving cavity 6, grommet 21 must be omitted.

Needle 15 will have an external diameter 26. Likewise, sheath 22 will have an external diameter 27. While preferred embodiments of both needle 15 and sheath 22 are generally cylindrical, it is recognized that both may have other shapes such that their cross-section is not a circle. In such cases, diameter is intended herein to refer to the longest cross-sectional dimension of the respective article unless otherwise indicated. External diameter 27 of sheath 22 at tip end 25 should be close enough to external diameter 26 of needle 15 to allow tip end 25 of sheath 22 to be inserted with needle 15 when safety syringe 1 is used. As needle 15 is inserted into tissue, it will create a puncture wound or tear in that tissue that is somewhat larger in diameter than external diameter 26 of needle 15. Sheath 22, and particularly tip end 25, should be sized to permit at least tip end 25 of sheath 22 to be inserted simultaneously with needle 15 into the puncture wound created by needle 15.

In designing sheath 22, there are two competing goals, strength or puncture resistance and patient comfort. The thinner sheath 22 is, the more comfortable it will be for the patient when sheath 22 is inserted with needle 15. However, as sheath 22 is made thinner, it becomes less resistant to punctures and thus less able to perform its task of preventing accidental sticks. Therefore, a balance must be struck between these two competing goals when sheath 22 is designed. Of course, where this balance will fall will depend upon the characteristics of the materials used to make sheath 22. Currently, the inventor contemplates using plastic, Teflon®, or a metal such as braided stainless steel. However, other acceptable rigid or semi-rigid substances may be available now or developed in the future which may affect the thickness of sheath 22. Furthermore, it is anticipated that a non-rigid substance such as soft rubber which relies on needle 15 for its rigidity during insertion would perform adequately as a substance from which sheath 22 might be constructed.

The thickness of sheath 22 will also vary with the size of needle 15. Needles come in twenty-five standard gauges, where gauge is a measure of external diameter 26. Standard needles range from 30 gauge which has an external diameter of $12/1000$ of an inch to 6 gauge which has an external diameter of $200/1000$ of an inch. The incremental change in diameter between gauges is not uniform. For example, 29 gauge has a diameter of $13/1000$ of an inch, only $1/1000$ more than 30 gauge. At the other end of the spectrum, 7 gauge has an outer diameter of $180/1000$ of an inch, $20/1000$ less than 6 gauge.

Although safety syringe 1 may be used with any size needle 15, needles in the middle of the standard needle range-24 to 18 gauge-are expected to be used most often. A 24 gauge needle has an external diameter of $22/1000$ while 18 gauge is $50/1000$. When needle 15 falls into this middle range, it is anticipated that sheath 22, or at least tip end 25, should have an external diameter 27 of not more than about 150% of external diameter 26 of needle 15. In this size range, it is anticipated that the external diameter 27 of sheath 22, or at least tip end 25, should preferably be between about 118% and about 125% of external diameter 26 of needle 15. With larger needles 15, such as 6 or 7 gauge, it is expected that sheath 22 or tip end 25 should have an external diameter 27 of not more than about 133% and preferably about 110% of external diameter 26 of needle 15. It should be appreciated that the construction and composition of sheath 22 may allow it to be made thinner than the ranges given above in furtherance of the goal of patient comfort. Similarly, different construction and composition may force sheath 22 to be thicker in order to satisfy the goal of puncture resistance.

A preferred embodiment of safety syringe 1 contains a means 34 for locking needle 15 out of extended position 23. In this preferred embodiment, the cross-section of plunger 10 has a shape that resembles a cross or an asterisk or other similar figure. The arms 28 of the cross extend substantially to interior wall 5. A pair of holes 29 are contained in interior wall 5. Holes 29 should be positioned near plunger end 4 of barrel 2 and should be positioned above the section of barrel 2 which ordinarily contains fluid receiving cavity 6. A pair of detents 30A and 30B are provided to snap-fit into holes 29. Detents 30 may be installed after plunger 10 and needle 15 have been installed in barrel 2. Detent 30A should have a beveled side 31 that faces away from detent 30 B. The sides of detents 30A and 30B which face each other, 32 and 33, should be substantially perpendicular to interior wall 5. In this preferred embodiment, washer end 12 of plunger 10 should be fixed to plunger 10 in a fashion that will not allow washer end 12 to rotate independently of plunger 10. Thus, turning plunger 10 will turn washer end 12 as well. Furthermore, needle 15 should extend from the center of washer end 12 of plunger 10, so that plunger 10 will turn on needle 15 when it is rotated about its longitudinal axis. Finally, locking means 34 comprises projection 13 and recess 14 as illustrated in FIGS. 2 and 3 and discussed above.

To use locking means 34, plunger 10 must only be rotated about its longitudinal axis after washer end 12 has been withdrawn far enough that the relative positions of projection 13 and recess 14 will allow such rotation. Upon rotation, arm 28 will contact beveled side 31 of detent 30A. The beveling will allow arm 28 to pass over detent 30A. However, once between detents 30A and 30B, further rotation in either direction will be prevented by detent sides 32 and 33. When arm 28 has been placed between detents 30A and 30B, plunger 10 and needle 15 are said to be in "locked" position 35.

In locked position 35, plunger 10 may be advanced to cause the emission of fluid from sheath 22, in much the same way that fluid is expelled from a conventional syringe. However, the rotation of plunger 10 will have taken projection 13 out of alignment with recess 14. This lack of alignment will block the forward progress of plunger 10 as washer end 12 approaches needle end 3. By appropriately sizing projection 13 and recess 14, the impedance to the forward motion of plunger 10 can prevent needle 15 from returning to extended position 23 in locked position 35.

In locked position 35, the retraction of plunger 10 may be continued if more fluid is to be collected. However, it is desirable that plunger 10 not be extracted completely from barrel 2 for several reasons. First, the vacuum in fluid receiving cavity 6 will be lost which will allow the contents of fluid receiving cavity 6 to escape. Second, extraction of plunger 10 from barrel 2 may cause needle 15 to be exposed after it has been contaminated. Third, retracting plunger 10 too far may cause needle 10 to be completely removed from sheath 22. This is undesirable because any movement of needle 15 at that point could prevent needle 15 from being reinserted into needle aperture 7 which would interfere with the advancement of plunger 10 and the expulsion of the contents of fluid receiving cavity 6.

Locking means 34 can also prevent excessive retraction of plunger 10. The rearward progress of plunger 10 will be checked when washer end 12 meets detents 30A and 30B. Thus, when plunger 10 is in locked position 35, needle 15 will be protectively encased within sheath 22 without impeding the ability to dispense the contents of fluid receiving cavity 6 by using plunger 10.

When safety syringe 1 is in this "locked" position 35, there will be some fluid which cannot be expelled because of the pocket created by recess 14. Minimizing the height of projection 13 and the corresponding depth of recess 14 will minimize the amount of fluid that will be retained. However, their height and depth must be sufficient to ensure that sharp end 16 of needle 15 will not be exposed when plunger 10 is fully depressed in locked position 35, yet still allow sharp end 16 to be exposed upon full depression when safety syringe is not in locked position 35.

In operation, the person collecting the fluids will sterilize the skin where the insertion is to be made. Then needle 15 and sheath 22, or at least tip end 25, will be injected into a body of fluid, such as a vein. Plunger 10 will be retracted which will cause a vacuum to be created in fluid receiving cavity 6 and will also cause needle 15 to move from extended position 23 to retracted position 24. The vacuum, and possibly the fluid's own pressure, will cause the fluid to flow through sheath 22 and needle 15 into fluid receiving cavity 6. Once the desired amount of fluid has been collected, safety syringe 1 may be removed from the patient. If the embodiment having locking means 34 is being used, the plunger should be rotated about its longitudinal axis until the syringe is placed in locked position 35. Tip end 25 of sheath 22 may then be placed where the operator wishes to expel the fluid. By depressing plunger 10, the fluid may be dispensed in a controlled fashion. Needle 15 is covered prior to removal from the patient, and when locking means 34 is used, safety syringe 1 may be used to dispense its contents in the same fashion as a conventional syringe without ever exposing sharp end 16 of needle 15. Once safety syringe 1 has been used, locking means 34 will prevent it from being reused and will also allow safety syringe 1 to be disposed without exposing needle 15 to human contact. Although safety syringe 1 may be used for blood collection, many other applications are contemplated by the inventor such as amniocentesis, spinal tap, needle biopsies of breast and other tissue, orthopedic applications such as joint fluid removal, or practically any other intracavity fluid sampling requiring a syringe.

It is anticipated that these and other uses and embodiments will be obvious to those skilled in the art and are intended to be covered by the scope of the following claims.

I claim:

1. A safety syringe comprising:
   a substantially hollow barrel having a needle end, a plunger end, and an interior wall extending between said plunger end and said needle end, wherein said needle end, said plunger end and said interior wall define a fluid receiving cavity within said barrel;
   a plunger extending from said fluid receiving cavity of said barrel, said plunger having a thumb end and a washer end, said washer end configured to create a substantially fluid tight seal between said washer end and said interior wall of said barrel, whereby operation of said plunger will vary the volume of said fluid receiving cavity;
   a retractable needle extending from said barrel, said needle having a sharp end, said needle providing fluid passage into said fluid receiving cavity, said needle having an extended position and a retracted position, said needle functionally connected to said plunger to allow said needle to be retracted upon operation of said plunger; and
   a hollow sheath circumferentially positioned over said needle, said sheath extending from said needle end of said barrel, said sheath having a tip end, said tip end having an external diameter, said tip end sized to be hypodermically insertable with said needle, said sheath sized so that said sharp end of said needle is exposed when said needle is in said extended position, said sheath further sized so that said sharp end of said needle is contained within said sheath when said needle is in said retracted position, said sheath configured to provide fluid passage to said needle when said needle is in said retracted position.

2. A safety syringe according to claim 1 wherein said tip end of said sheath has an external diameter of not more than about 150% of said external diameter of said needle.

3. A safety syringe according to claim 1 wherein said tip end of said sheath has an external diameter of not more than about 133% of said external diameter of said needle.

4. A safety syringe according to claim 1 wherein said tip end of said sheath has an external diameter that is between about 118% and about 125% of said external diameter of said needle.

5. A safety syringe according to claim 1 wherein said tip end of said sheath has an external diameter of about 110% of said external diameter of said needle.

6. A safety syringe according to claim 1 wherein said tip end has cross-sectional dimensions wherein the shortest cross-sectional dimension of said tip end is less than the longest cross-sectional dimension of a puncture wound createable by said needle during hypodermic injection.

7. A safety syringe according to claim 1 wherein said tip end has cross-sectional dimensions wherein the longest cross-sectional dimension of said tip end is less than the longest cross-sectional dimension of a puncture wound createable by said needle during hypodermic injection.

8. A safety syringe according to claim 1 further comprising a means for locking said needle out of said extended position.

9. A safety syringe according to claim 8 wherein said tip end of said sheath has an external diameter of not more than about 150% of said external diameter of said needle.

10. A safety syringe according to claim 8 wherein said tip end of said sheath has an external diameter of not more than about 133% of said external diameter of said needle.

11. A safety syringe according to claim 8 wherein said tip end of said sheath has an external diameter that is between about 118% and about 125% of said external diameter of said needle.

12. A safety syringe according to claim 8 wherein said tip end of said sheath has an external diameter of about 110% of said external diameter of said needle.

13. A safety syringe according to claim 8 wherein said tip end has cross-sectional dimensions wherein the shortest cross-sectional dimension of said tip end is less than the longest cross-sectional dimension of a puncture wound createable by said needle during hypodermic injection.

14. A safety syringe according to claim 8 wherein said tip end has cross-sectional dimensions wherein the longest cross-sectional dimension of said tip end is less than the longest cross-sectional dimension of a puncture wound createable by said needle during hypodermic injection.

15. A safety syringe according to claim 1 further comprising a projection extending from said washer end of said plunger and a recess contained within said needle end of said barrel sized to receive said projection.

16. A safety syringe according to claim 15 wherein said tip end of said sheath has an external diameter of not more than about 150% of said external diameter of said needle.

17. A safety syringe according to claim 15 wherein said tip end of said sheath has an external diameter of not more than about 133% of said external diameter of said needle.

18. A safety syringe according to claim 15 wherein said tip end of said sheath has an external diameter that is between about 118% and about 125% of said external diameter of said needle.

19. A safety syringe according to claim 15 wherein said tip end of said sheath has an external diameter of about 110% of said external diameter of said needle.

20. A safety syringe according to claim 15 wherein said tip end has cross-sectional dimensions wherein the shortest cross-sectional dimension of said tip end is less than the longest cross-sectional dimension of a puncture wound createable by said needle during hypodermic injection.

21. A safety syringe according to claim 15 wherein said tip end has cross-sectional dimensions wherein the longest cross-sectional dimension of said tip end is less than the longest cross-sectional dimension of a puncture wound createable by said needle during hypodermic injection.

* * * * *